US00PP30282P3

(12) United States Plant Patent
Kubo et al.

(10) Patent No.: US PP30,282 P3
(45) Date of Patent: Mar. 5, 2019

(54) CAULIFLOWER MUSHROOM NAMED 'SHIROBANABIJIN'

(50) Latin Name: ***Sparassis crispa* (Wulfen):Fr.**
Varietal Denomination: Shirobanabijin

(71) Applicants: Masahide Kubo, Ito-gun, Wakayama (JP); Takahiro Kubo, Hashimoto-shi, Wakayama (JP)

(72) Inventors: Masahide Kubo, Ito-gun (JP); Takahiro Kubo, Hashimoto (JP); Atsuki Ikeda, Wakayama (JP)

(73) Assignees: Masahide Kubo, Wakayama (JP); Takahiro Kubo, Wakayama (JP)

( * ) Notice: Subject to any disclaimer, the term of this patent is extended or adjusted under 35 U.S.C. 154(b) by 0 days.

(21) Appl. No.: 15/731,743

(22) Filed: Jul. 27, 2017

(65) Prior Publication Data

US 2018/0220572 P1 Aug. 2, 2018

(51) Int. Cl.
*A01H 15/00* (2006.01)
*C12N 1/16* (2006.01)

(52) U.S. Cl.
USPC ..... Plt./394
CPC ..... *A01H 15/00* (2013.01); *C12N 1/16* (2013.01)

(58) Field of Classification Search
USPC ..... Plt./394
CPC ..... A01H 15/00; C12N 1/14
See application file for complete search history.

(56) References Cited

PUBLICATIONS

Kubo, "KSC-H2GO", Ministry of Agriculture, Forestry and Fisheries of Japan, Jul. 31, 2009, cited in Specification, w/English translation (2 pages).
Kubo et al., "KSC-H5GO", Ministry of Agriculture, Forestry and Fisheries of Japan, Mar. 18, 2011, cited in Specification, w/English translation (2 pages).
Kubo et al., "KSC-H7GO", Ministry of Agriculture, Forestry and Fisheries of Japan, May 15, 2014, cited in Specification, w/English translation (2 pages).

*Primary Examiner* — June Hwu
(74) *Attorney, Agent, or Firm* — Westerman, Hattori, Daniels & Adrian, LLP

(57) ABSTRACT

The claimed cauliflower mushroom plant named 'Shirobanabijin' has a higher primordium forming ability and a higher differentiating ability and, hence, higher productivity, higher production stability and higher crop yield. Further, the fruit body of 'Shirobanabijin' has a greater branch thickness and a moderately resilient flesh texture and, therefore, is less susceptible to breakage and shape collapse of petals and branches in the harvesting and the packaging thereof. Thus, 'Shirobanabijin' ensures efficient workability in the harvesting and the packaging. In addition, 'Shirobanabijin' is white as compared with existing varieties.

15 Drawing Sheets

Latin name of the genus and species of the plant claimed: *Sparassis crispa* (Wulfen):Fr.

Variety denomination: Cauliflower mushroom 'Shirobanabijin'.

BACKGROUND OF THE INVENTION

The present invention relates to a new and distinct variety of cauliflower mushroom plant named 'Shirobanabijin' which is characterized by higher productivity, higher production stability, higher crop yield, efficient workability and higher product quality.

A cauliflower mushroom is generally white to pale yellow, and shaped like Acropora coral. The cauliflower mushroom grows on roots and stumps of coniferous trees such as larch trees in nature in summer and autumn. The fruit body of the cauliflower mushroom includes a stipe, branches and petals.

The cauliflower mushroom requires a cultivation period of about 3 months, which is about twice the cultivation periods of a conventional eryngii mushroom and maitake mushroom. Further, the cauliflower mushroom is unstable in crop yield and product quality and susceptible to contamination with unwanted bacteria, and has a lower fruiting percentage (or is often unable to develop fruit bodies.) This makes it difficult to mass-produce the cauliflower mushroom.

The inventors conducted intensive studies to solve the problems described above and, as a result, developed cauliflower mushroom varieties named 'KSC-H2' (Japanese Plant Variety Registration No. 18362) and 'KSC-H7' (Japanese Plant Variety Registration No. 28767).

'KSC-H2' has a higher productivity and, therefore, requires a shorter cultivation period. However, the fruit body of 'KSC-H2' is pale yellow. In general, white mushrooms are favored in the United States of America, and account for 63% of mushrooms on sale in the market. (see www.mushroomcouncil.org/topline-reports)

In view of the foregoing, 'KSC-H2' still requires improvement.

'KSC-H7' has a higher productivity, and requires a shorter cultivation period. However, the branches of the fruit body of 'KSC-H7' are very thick, and have hard flesh texture. Therefore, the branches and the petals of 'KSC-H7' are liable to be broken in the harvesting and the packaging of the fruit body. Thus, 'KSC-H7' still requires improvement.

The inventors further conducted intensive studies to provide a further improved cultivar and, finally, developed the claimed 'Shirobanabijin'.

The claimed 'Shirobanabijin' is a cauliflower mushroom variety produced by crossbreeding Japanese registered cauliflower mushroom varieties 'KSC-H2' and 'KSC-H5' (Registration No. 20728) and further crossbreeding the resulting variety 'KSC-H7' and 'KSC-H2' (see FIG. 1). More specifically, 'Shirobanabijin' was produced through the following crossbreeding and cultivating process:

1) In May 2004, fruit bodies were isolated from two wild strains sampled in Nagano, Japan, and crossbred. The resulting strain was named 'KSC-H2'.
2) In January 2009, fruit bodies were isolated from other two wild strains sampled in Nagano, Japan, and crossbred. The resulting strain was named 'KSC-H5'.
3) In August 2012, 'KSC-H2' and 'KSC-H5' were crossbred. The resulting strain was named 'KSC-H7'.
4) In December 2016, 'KSC-H7' and 'KSC-H2' were crossbred. Thus, the claimed 'Shirobanabijin' was obtained.
5) From December 2016 to April 2017, an extensive cultivation test of the 'Shirobanabijin' strain was performed in Koyaguchi-cho, Hashimoto-Shi, Wakayama, Japan, and it was confirmed that 'Shirobanabijin' has stable characteristics. The claimed 'Shirobanabijin' was produced by crossbreeding 'KSC-H7' and 'KSC-H2'. The crossbreeding was conducted on the PDA medium dispensed in culture dishes. The details are as follows:

I. The strain obtained by the crossbreeding was aseptically inoculated on sterilized PDA medium dispensed in culture dishes, which were kept in a freezer.

II. The medium prepared by mixing the base material, the nutrients, and water was filled in polyethylene cultivation bottles having a mouth diameter of 58 mm and a volume of 850 mL. The polyethylene cultivation bottles filled with the medium were sterilized by a high-pressure steam sterilization method, and then cooled.

III. Pieces of the PDA medium having mycelia were aseptically cut out from the strain of step I and inoculated on the medium of step II so that the mycelia spreads on the medium.

IV. Further, another medium of step II was inoculated with the medium of step III so that the mycelia spreads on the medium.

V. Further, another medium of step II was inoculated with the medium of step IV so that the mycelia spreads on the medium, which was obtained as a fungal spawn.

VI. Another medium of step II was inoculated with the fungal spawn of step V and was cultured and grown to be harvested and subjected to characteristic evaluations. This whole cultivation is called a "course," and three courses were conducted to confirm that 'Shirobanabijin' has stable characteristics.

An asexually reproduced clone of the claimed variety obtained from the extensive cultivation test is identical to the original claimed variety in all distinguishing characteristics.

SUMMARY OF THE INVENTION

Noticeable characteristics of the claimed variety 'Shirobanabijin' are as follows:

1. 'Shirobanabijin' has higher productivity with a shorter cultivation period than existing varieties.
2. 'Shirobanabijin' ensures higher production stability and higher crop yield than the existing varieties.
3. 'Shirobanabijin' is less susceptible to breakage of petals and branches thereof and shape collapse thereof and, therefore, ensures more efficient workability in the harvesting and the packaging of fruit bodies thereof, because the branches of the fruit bodies are moderately thick and moderately resilient in flesh texture as compared with the existing varieties.
4. The fruit bodies of 'Shirobanabijin' are entirely white as compared with the existing varieties.

BRIEF DESCRIPTION OF DRAWINGS

FIG. 1 is a genealogical chart for 'Shirobanabijin'.

FIG. 2 is a photograph showing a state of 'Shirobanabijin' on the 14th culturing day.

FIG. 3 is a photograph showing a state of 'KSC-H7' on the 14th culturing day.

FIG. 4 is a photograph showing a state of 'KSC-H2' on the 14th culturing day.

FIG. 5 is a photograph showing an example of fruit bodies of central fruiting type.

FIG. 6 is a photograph showing an example of fruit bodies of overall fruiting type.

FIG. 7 is a photograph showing an example of fruit bodies of peripheral fruiting type.

FIG. 8 is a photograph showing the fruiting type of 'Shirobanabijin'.

FIG. 9 is a photograph showing the fruiting type of 'KSC-H7'.

FIG. 10 is a photograph showing the fruiting type of 'KSC-H2'.

FIG. 11 is a graph showing a relationship between the number of fungal beds and a period from inoculation to a fruiting operation possible day for 'Shirobanabijin', 'KSC-H7' and 'KSC-H2'.

FIG. 12 is a diagram showing designations of parts of a fruit body, in which A designates a petal, B designates a branch, C designates a stipe, D designates a stipe thickness measurement part, and E designates a branch thickness measurement part.

FIG. 13 is a photograph showing standards of the major diameter i and the minor diameter ii of a fruit body.

FIG. 14 is a photograph showing a standard of the height of a fruit body.

FIG. 15 is a photograph showing an example of a spine-type petal of a fruit body.

FIG. 16 is a photograph showing an example of a carnation-type petal of a fruit body.

FIG. 17 is a photograph showing an example of a kale-type petal of a fruit body.

FIG. 18 is a photograph showing an example of a ginkgo-type petal of a fruit body.

FIG. 19 is a photograph showing the color of a stipe of 'Shirobanabijin'.

FIG. 20 is a photograph showing the color of a stipe of 'KSC-H7'.

FIG. 21 is a photograph showing the color of a stipe of 'KSC-H2'.

FIG. 22 is a photograph showing the color of branches of 'Shirobanabijin'.

FIG. 23 is a photograph showing the color of branches of 'KSC-H7'.

FIG. 24 is a photograph showing the color of branches of 'KSC-H2'.

FIGS. 25A and 25B are photographs showing a top view and a bottom view, respectively, of dual culture of 'Shirobanabijin'.

FIGS. 26A and 26B are photographs showing a top view and a bottom view, respectively, of dual culture of 'Shirobanabijin' and 'KSC-H7'.

FIGS. 27A and 27B are photographs showing a top view and a bottom view, respectively, of dual culture of 'Shirobanabijin' and 'KSC-H2'.

DETAILED BOTANICAL DESCRIPTION

The characteristics of 'Shirobanabijin' will be described in comparison with existing varieties, i.e., a variety 'KSC-H7' applied for plant variety registration in Japan and a Japanese registered variety 'KSC-H2'.

Cultivation of Cauliflower Mushroom

'Shirobanabijin', 'KSC-H7' and 'KSC-H2' were cultivated in the following manner, and evaluated for primordium forming ability, fruiting type, fruiting period, differentiating ability, crop yield, cultivation period and fruit body morphological characteristics. The term "primordium" herein means a white lump from which a fruit body of the cauliflower mushroom is developed. The primordium grows into a stipe, branches and petals of the cauliflower mushroom (this process is hereinafter referred to as "differentiation").

The fruit bodies of these varieties for the comparison test were cultivated from February 2017 to April 2017.

Polyethylene cultivation bottles (each having a mouth diameter of 58 mm and a volume of 850 mL) were used for the cultivation. For preparation of medium, sawdust of coniferous trees such as larch trees and Oregon pine trees were used as a base material, and wheat bran, flour, barley and beer yeast were used as nutrients. The medium was prepared by mixing 18 to 25 parts by weight of the wheat bran and the flour, 5 to 8 parts by weight of the barley and 2 to 4 parts by weight of the beer yeast with 100 parts by weight of the coniferous tree sawdust on a dry weight basis, and controlling the water content of the resulting mixture at 65±2%. The polyethylene cultivation bottles were each filled with the medium, which was in turn sterilized by a high-pressure steam sterilization method. The bottles of medium thus sterilized were cooled to a temperature of not higher than 20° C. in a clean room, and the bottles of medium were each inoculated with about 10 to about 15 g of fungal spawn. The bottles of medium each inoculated with the fungal spawn (hereinafter referred to as "fungal beds") were cultured at a temperature of 21±3° C. at a humidity of 60 to 80% at a carbon dioxide concentration of not higher than 4,000 ppm until primordia were formed to allow for a fruiting operation (differentiation start time).

Subsequently, the fungal beds to be subjected to the fruiting operation were maintained at a temperature of 18±3° C. at a humidity of 90 to 95% at a carbon dioxide concentration of not higher than 4,000 ppm in light, whereby the fruiting was promoted.

Thereafter, the fruit bodies were harvested before spores were formed in sporophores (petals). The medium was removed from stipe bases of the fruit bodies and, in this state, measurement was performed on the fruit bodies.

In the cultivation, 3 batches each including 32 such cultivation bottles (96 cultivation bottles in total) were employed for each of the varieties.

In the test, the polyethylene cultivation bottles were used for the cultivation, but the claimed 'Shirobanabijin' may be cultivated in polyethylene cultivation bags which are commonly used for the fungal bed cultivation of mushrooms. In this case, the cultivation may be performed under the same cultivation conditions as employed for the cultivation in the cultivation bottles. The fruit bodies obtained from the cultivation bottles and fruit bodies obtained from the cultivation bags have no difference in morphological characteristics and the like, and provide the similar results.

The fruit bodies thus produced were each evaluated for the following evaluation items.

Primordium Forming Ability

The polyethylene bottles were visually observed to determine when the primordium formation of the cauliflower mushroom started after the culturing.

The primordium formation of the claimed 'Shirobanabijin' started after a lapse of about 2 weeks from the start of the culturing. In contrast, the primordium formation of 'KSC-H7' started after a lapse of about 3 weeks from the start of the culturing, and the primordium formation of 'KSC-H2' started after a lapse of about 2 weeks from the start of the culturing (see FIGS. 2 to 4). It was confirmed that the claimed 'Shirobanabijin' has substantially the same primordium formation starting period as 'KSC-H2', which has a higher primordium forming ability. Thus, the claimed 'Shirobanabijin' has a higher primordium forming ability and, hence, a higher fruiting percentage and a shorter cultivation period.

Fruiting Type and Fruiting Period

The fruiting type (fruiting state) of the cauliflower mushroom was visually observed. The fruiting type was classified as "central fruiting type" when fruit bodies were developed on a center surface portion of the fungal bed as shown in FIG. 5, classified as "overall fruiting type" when fruit bodies were developed on the overall surface of the fungal bed as shown in FIG. 6, or classified as "peripheral fruiting type" when fruit bodies were developed on a peripheral surface portion of the fungal bed as shown in FIG. 7. Further, a period from the inoculation to the fruiting operation possible day and the number of fungal beds are shown below in Table 1.

TABLE 1

(Period from inoculation to fruiting operation possible day and number of fungal beds)

| Period | Shirobanabijin | KSC-H7 | KSC-H2 |
|---|---|---|---|
| 32 days | 8 | 0 | 0 |
| 33 days | 20 | 3 | 0 |
| 34 days | 32 | 21 | 12 |
| 35 days | 31 | 30 | 49 |
| 36 days | 5 | 0 | 4 |
| 37 days | 0 | 7 | 3 |
| 38 days | 0 | 15 | 12 |
| 39 days | 0 | 13 | 16 |
| 40 days | 0 | 7 | 0 |

The claimed 'Shirobanabijin' was of the overall fruiting type. 'KSC-H7' was of the overall fruiting type or the peripheral fruiting type, and 'KSC-H2' was of the overall fruiting type (see FIGS. 8 to 10). As shown in Table 1 and FIG. 11, 'KSC-H7' and 'KSC-H2' each have two peaks with respect to the period from the inoculation to the fruiting operation possible day, while the claimed 'Shirobanabijin' has a single peak with respect to the period from the inoculation to the fruiting operation possible day. This means that the fungal beds of the claimed 'Shirobanabijin' can be simultaneously subjected to the fruiting operation. Thus, the claimed 'Shirobanabijin' is stable in primordium formation time, primordium growth rate and differentiation speed and, therefore, has higher productivity.

Differentiating Ability

The differentiation of the developed fruit bodies of the cauliflower mushroom was visually observed.

The differentiation of the claimed 'Shirobanabijin' was started simultaneously with the fruiting (see FIG. 8). 'KSC-H7' was lower in differentiation degree than the claimed 'Shirobanabijin' (see FIG. 9), and 'KSC-H2' was comparable in differentiation degree to the claimed 'Shirobanabijin' (see FIG. 10). The claimed 'Shirobanabijin' had substantially the same differentiating ability as 'KSC-H2' which has a higher differentiating ability. Therefore, it is considered that the claimed 'Shirobanabijin' also has a higher differentiating ability and, hence, is highly stable in fruit body morphology and requires a shorter cultivation period.

Cultivation Period

The total cultivation periods in days (the culturing period plus the fruiting period) of the claimed variety and the comparative varieties are shown below in Table 2.

TABLE 2

(Total cultivation period of cauliflower mushroom)

| | Shirobanabijin | KSC-H7 | KSC-H2 |
|---|---|---|---|
| Culturing period | 34.1 | 36.2 | 36.0 |
| Fruiting period | 17.5 | 17.9 | 21.6 |
| Total cultivation period | 51.6 | 54.1 | 57.6 |

As shown above in Table 2, the claimed 'Shirobanabijin' required a shorter culturing period and a shorter fruiting period and, hence, a shorter total cultivation period than the comparative varieties 'KSC-H7' and 'KSC-H2'.

The above evaluation results for the primordium forming ability, the fruiting type and the fruiting period, the differentiating ability and the cultivation period indicate that the claimed 'Shirobanabijin' has higher productivity.

Crop Yield

The crop yield of the harvested cauliflower mushroom was measured. The results of the measurement are shown below in Table 3.

TABLE 3

(Crop yield of cauliflower mushroom)

| Crop yield | Shirobanabijin | KSC-H7 | KSC-H2 |
|---|---|---|---|
| Less than 100 g | 0 | 8 | 7 |
| 100 g to less than 110 g | 0 | 7 | 11 |
| 110 g to less than 120 g | 5 | 39 | 28 |
| 120 g to less than 130 g | 28 | 33 | 40 |
| 130 g to less than 140 g | 46 | 8 | 10 |
| 140 g or more | 17 | 1 | 0 |

As shown in Table 3, 'KSC-H7' and 'KSC-H2' each had greater variations in crop yield, but the claimed 'Shirobanabijin' had smaller variations in crop yield. The average crop yield of 'Shirobanabijin' was 133.2 g. The average crop yield of 'KSC-H7' was 117.4 g, and the average crop yield of 'KSC-H2' was 118.2 g. Thus, the claimed 'Shirobanabijin' had a greater crop yield than the comparative varieties. This means that the claimed 'Shirobanabijin' has higher production stability and higher crop yield.

Morphological Characteristics of Fruit Body

From each batch, 10 cultivation bottles containing fruit bodies having average morphological characteristics were selected, and the dimensions of the fruit bodies were measured and averaged for determination of the morphological characteristics of the fruit bodies.

For determination of the diameter of the fruit body, the major diameter and the minor diameter of the fruit body were measured and averaged (see FIG. 13).

The height of the fruit body was determined as measured from the mouth of the cultivation bottle to the apex of a petal of the fruit body (see FIG. 14).

For determination of the thickness of the stipe, the thickness of a portion of the stipe just below branches was measured (see FIG. 12).

The number of branches having a length of not smaller than 5 cm from their bases was determined.

The petals of the fruit body were visually observed for determination of the petal shape. The petal shape was classified as "spine type" when the petal had a shape as shown in FIG. 15, classified as "carnation type" when the petal had a shape as shown in FIG. 16, classified as "kale type" when the petal had a shape as shown in FIG. 17, or classified as "ginkgo type" when the petal had a shape as shown in FIG. 18.

For determination of the thickness of the branch, the thickness of a 5- to 10-mm long portion of the branch from a distal end of the petal was measured (see FIG. 12).

The fruit body was evaluated for the flesh textures of the stipe and the branch thereof by pinching the stipe and the branch with fingers. The flesh texture of the stipe or the branch was classified as "soft" when the stipe or the branch had a lower hardness than that of a reference variety 'NBRC102492', classified as "intermediate" when the stipe or the branch had substantially the same hardness as that of 'NBRC102492' or classified as "hard" when the stipe or the branch had a higher hardness than that of 'NBRC102492'.

The reference variety 'NBRC102492' is a cauliflower mushroom plant deposited with Japan's National Institute of Technology and Evaluation. In addition, the variety 'NBRC102492' is used as a reference variety in the present specification because the variety 'NBRC102492' is also used as the reference variety in the Examination Guidelines for Variety Registration of 'Cauliflower Mushroom' issued by the Japan Ministry of Agriculture, Forestry and Fisheries.

The results are shown below in Table 4.

TABLE 4

(Morphological characteristics of fruit body)

| Morphology | Shirobanabijin | KSC-H7 | KSC-H2 |
|---|---|---|---|
| Fruit body diameter (cm) | 12.8 | 12.7 | 12.6 |
| Fruit body height (cm) | 9.8 | 9.9 | 10.7 |
| Stipe thickness (mm) | 2.2 | 2.3 | 2.2 |
| Number of fruit body branches | 2.9 | 2.9 | 2.6 |
| Fruit body petal shape | Kale type | Kale type | Kale type |
| Fruit body branch thickness (mm) | 1.5 | 2.1 | 0.7 |
| Stipe Flesh texture | Intermediate | Intermediate | Intermediate |
| Fruit body branch flesh texture | Intermediate | Hard | Soft |

The claimed 'Shirobanabijin' was substantially the same in fruit body diameter, fruit body height, stipe thickness, the number of fruit body branches and stipe flesh texture as the comparative varieties 'KSC-H7' and 'KSC-H2'. The claimed 'Shirobanabijin' had the same fruit body petal shape as the comparative varieties 'KSC-H7' and 'KSC-H2'.

The fruit body branch of the claimed 'Shirobanabijin' was thick and had an intermediate flesh texture. In contrast, the fruit body branch of 'KSC-H7' was very thick and had a hard flesh texture, and the fruit body branch of 'KSC-H2' was thin and had a soft flesh texture.

In general, the petals and the branches of the cauliflower mushroom have substantially the same morphological tendency (thickness and flesh texture). The morphology of the petals and the branches significantly influences the workability in the harvesting and the packaging. More specifically, a fruit body having a greater branch thickness and a harder branch flesh texture is more susceptible to breakage of its petals and branches when even a small physical impact is applied to the fruit body in the harvesting and the packaging, and a cauliflower mushroom with its petals and branches thus broken loses its commercial value. Further, a fruit body having a smaller branch thickness and a softer branch flesh texture is more susceptible to shape collapse in the harvesting and the packaging, and a cauliflower mushroom suffering from shape collapse loses its commercial value.

Therefore, the claimed 'Shirobanabijin' which has a fruit body with a moderate branch thickness and a moderate branch flesh texture ensures efficient workability in the harvesting and the packaging.

Observation of Colors of Stipe and Branches of Fruit Body

The colors of the stipe and the branches of the fruit body were visually observed. Incidentally, in cauliflower mushrooms, a color of branches and a color of petals are usually same. The results are shown below in Table 5.

The color designations herein used are based on The Colour Chart specified by The Royal Horticultural Society (The Royal Horticultural Society (R.H.S.) London, Sixth Edition (2015)).

TABLE 5

(Colors of stipe and branches of fruit body)

| | Shirobanabijin | KSC-H7 | KSC-H2 |
|---|---|---|---|
| Stipe | Yellowish white (RHS No. 158C) | Pale yellow (RHS No. 11D) | Pale greenish yellow (RHS No. 10D) |
| Branches | Yellowish white (RHS No. 155B) | Pale yellow (RHS No. 158B) | Light yellow (RHS No. 10C) |

The color of the stipe of the claimed 'Shirobanabijin' was yellowish white (RHS No. 158C). In contrast, the color of the stipe of 'KSC-H7' was pale yellow (RHS No. 11D), and the color of the stipe of 'KSC-H2' was pale greenish yellow (RHS No. 10D) (see FIGS. 19 to 21).

The color of the branches of the claimed 'Shirobanabijin' was yellowish white (RHS No. 155B). In contrast, the color of the branches of 'KSC-H7' was pale yellow (RHS No. 158B), and the color of the branches of 'KSC-H2' was light yellow (RHS No. 10C) (see FIGS. 22 to 24).

Thus, the fruit body of the claimed 'Shirobanabijin' is entirely white as compared with the comparative varieties.

Dual Culture Test

Potato dextrose ager (PDA) medium was sterilized at 121° C. for 15 minutes by an ordinary high-pressure steam sterilization method. The sterilized medium was dispensed in culture dishes for preparation of flat media. Dikaryotic mycelia of 'Shirobanabijin', 'KSC-H7' and 'KSC-H2' were each pre-cultured on another PDA medium (at 25±1° C. for 20 to 30 days). Dual culture was performed by inoculating small pieces of the dikaryotic mycelia of these varieties in 30±5 mm spaced and juxtaposed relation on the flat medium in the culture dish and culturing the mycelia at 25±2° C. When the resulting two colonies contacted each other, the culture dish was exposed to light at an illuminance of 100 to 300 lux or higher at 25±1° C. The culture dish was checked for formation of an inhibition zone. The results are shown below in Table 6.

TABLE 6

(Results of dual culture with respect to 'Shirobanabijin')

| | Shirobanabijin | KSC-H7 | KSC-H2 |
|---|---|---|---|
| Formation of inhibition zone | − | + | + |

−: Inhibition zone was not formed.
+: Inhibition zone was formed.

The results shown above in Table 6 indicate that the inhibition zone (antagonistic line) was formed between 'Shirobanabijin' and the comparative varieties. Thus, it was confirmed that 'Shirobanabijin' is genetically different from the comparative varieties (see FIGS. 25A to 27B).

What is claimed is:

1. A new and distinct variety of cauliflower mushroom named 'Shirobanabijin' as substantially illustrated and described herein.

【FIG.1】
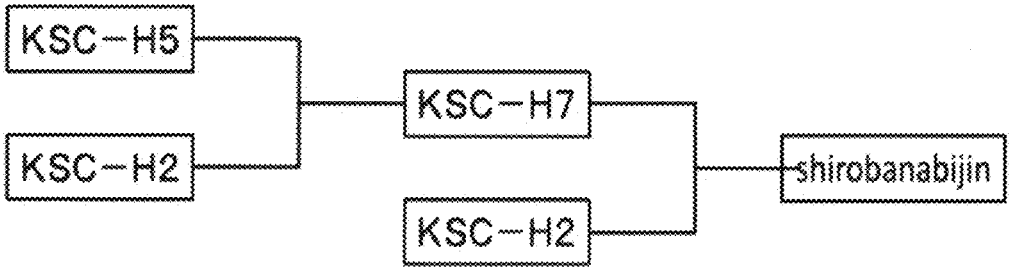
【FIG.2】
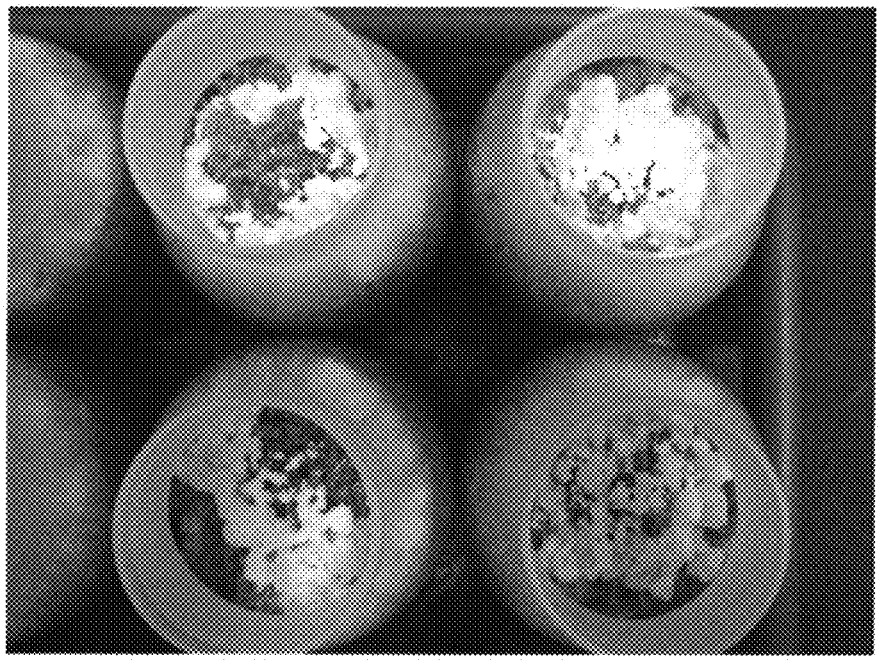

【FIG.3】
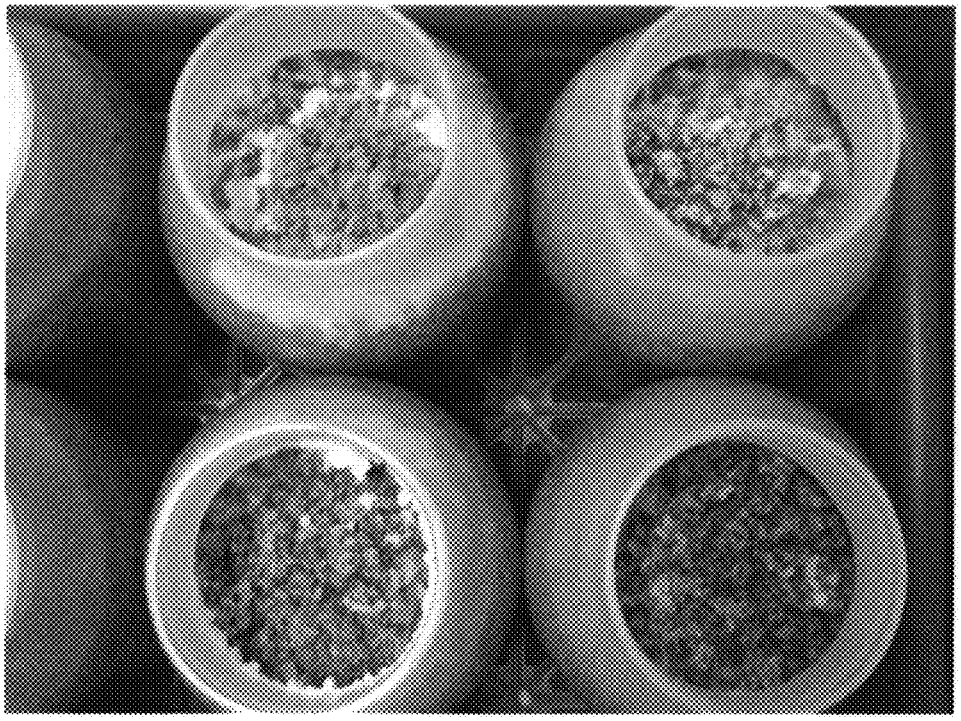
【FIG.4】
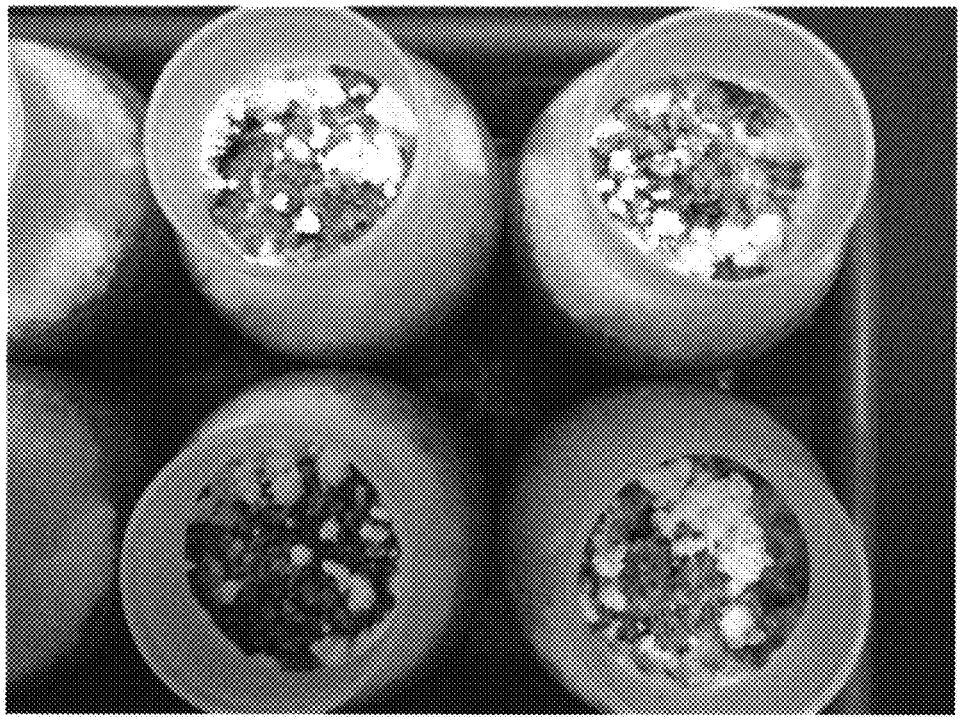

【FIG.5】
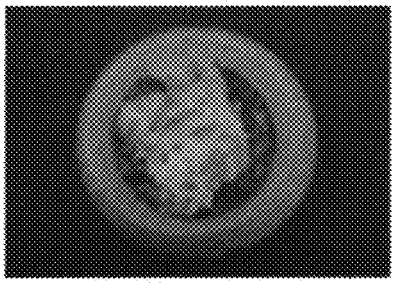
【FIG.6】
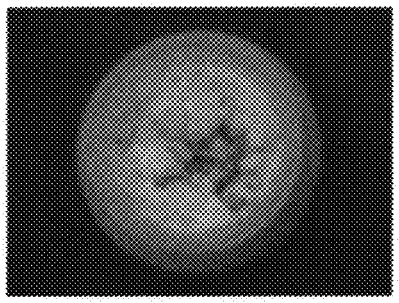
【FIG.7】
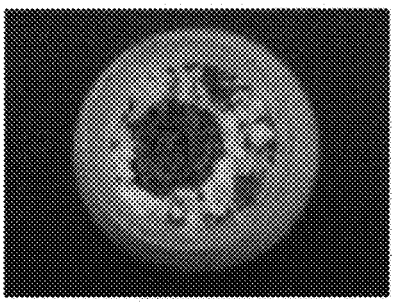

【FIG.8】
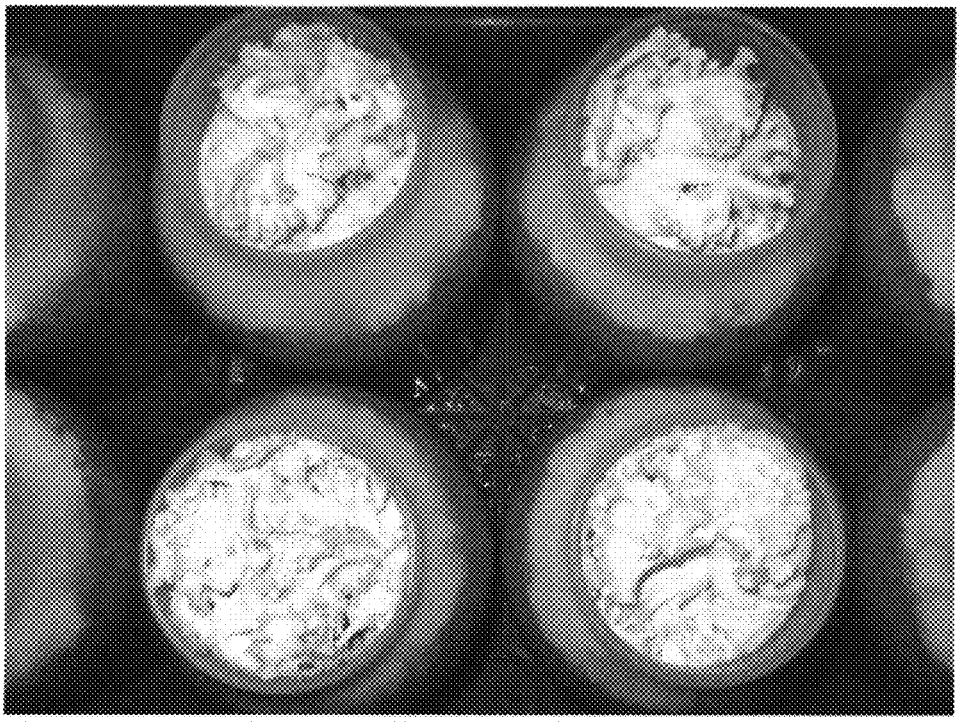
【FIG.9】
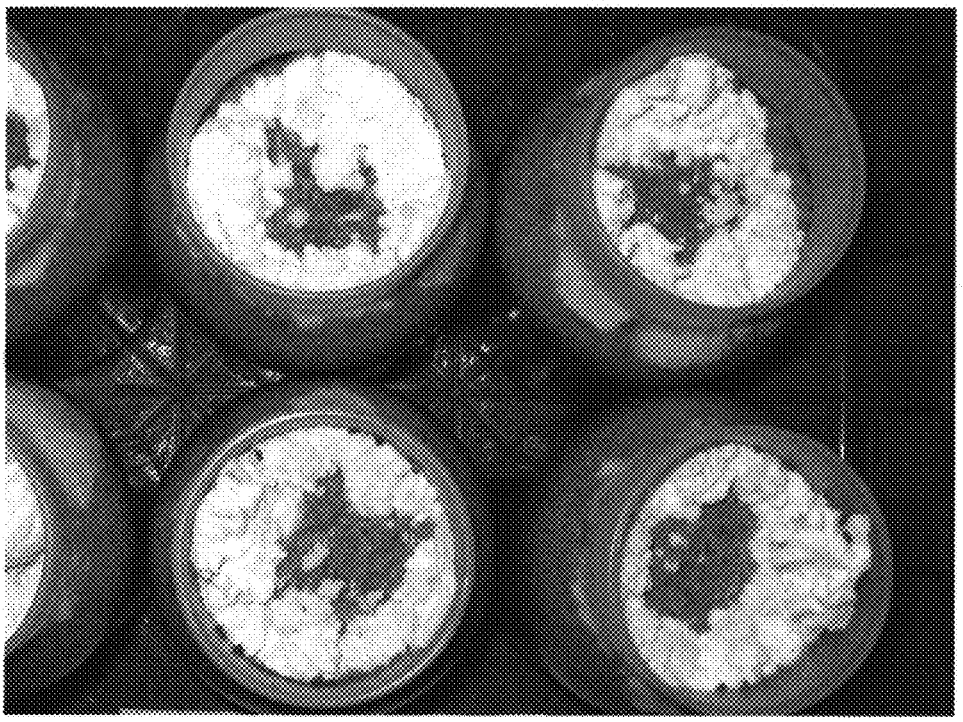

【FIG.10】
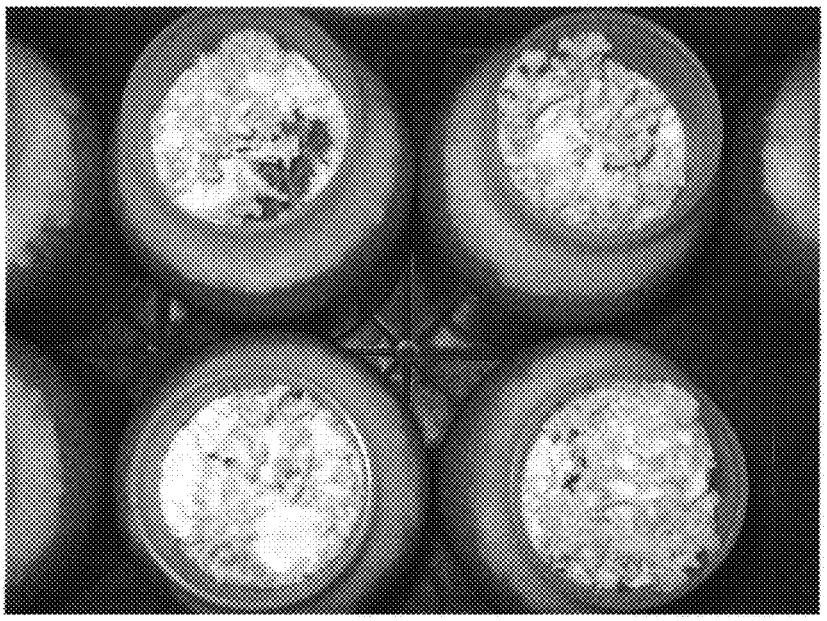
【FIG.11】
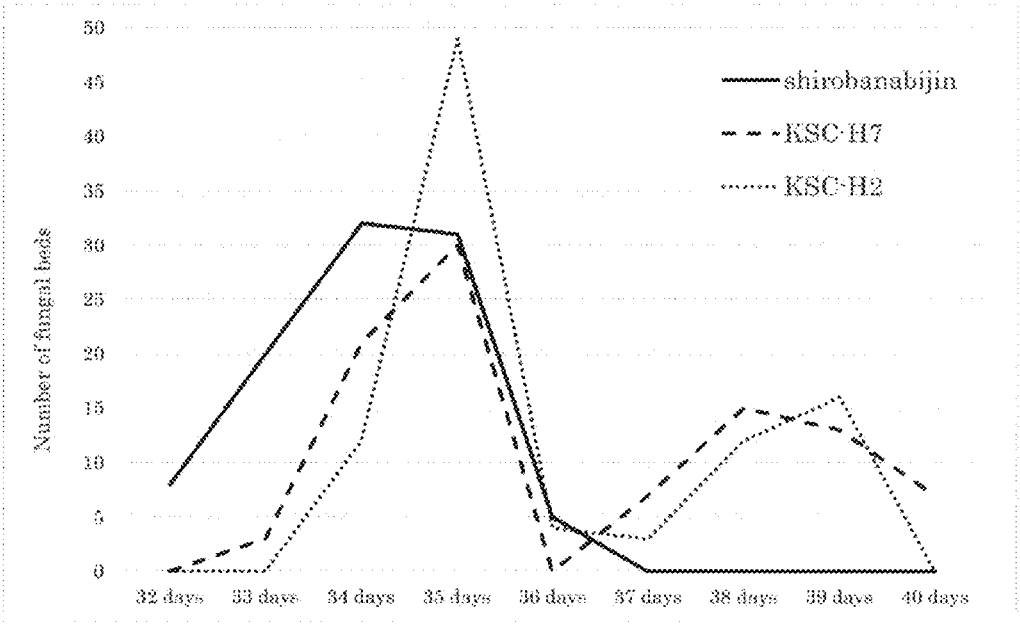

【FIG.12】
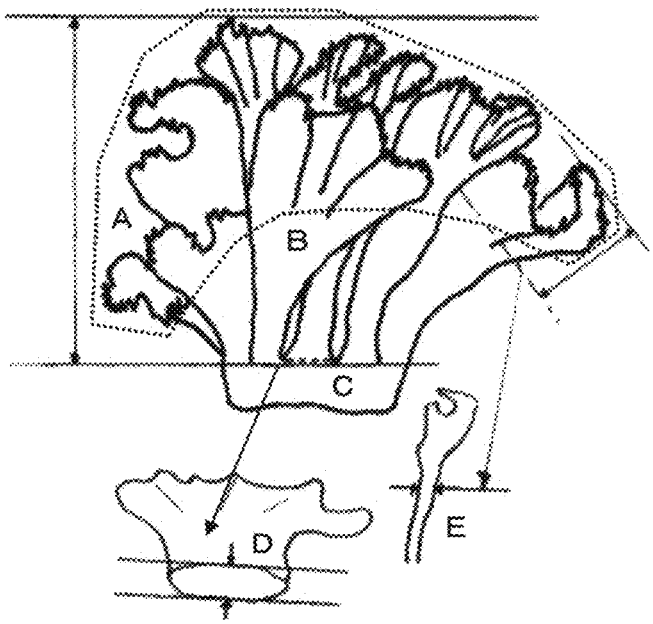
【FIG.13】
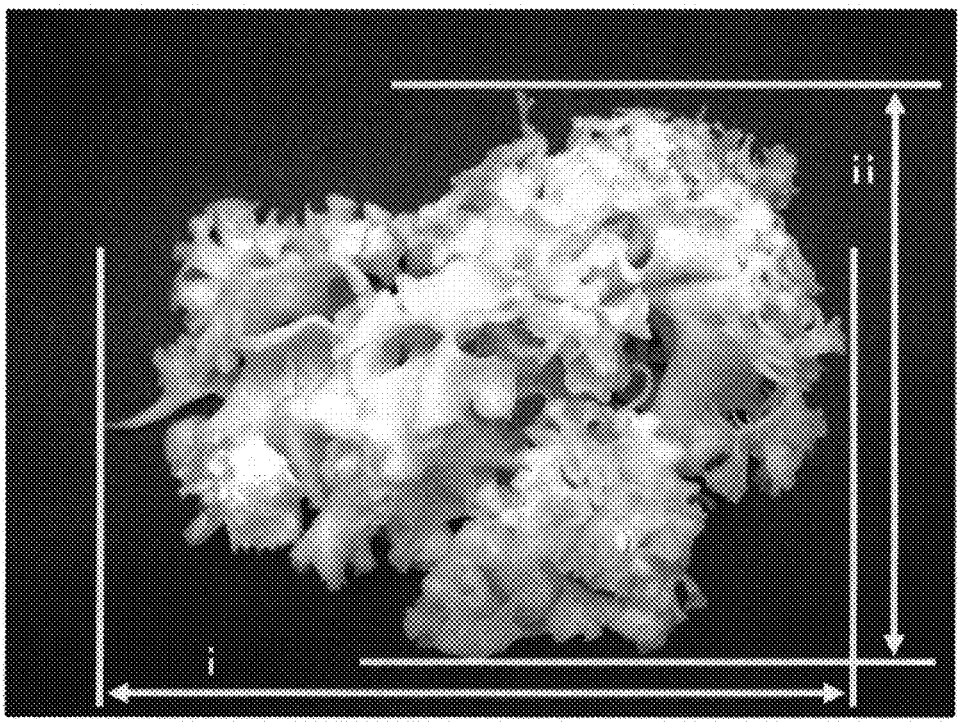

【FIG.14】
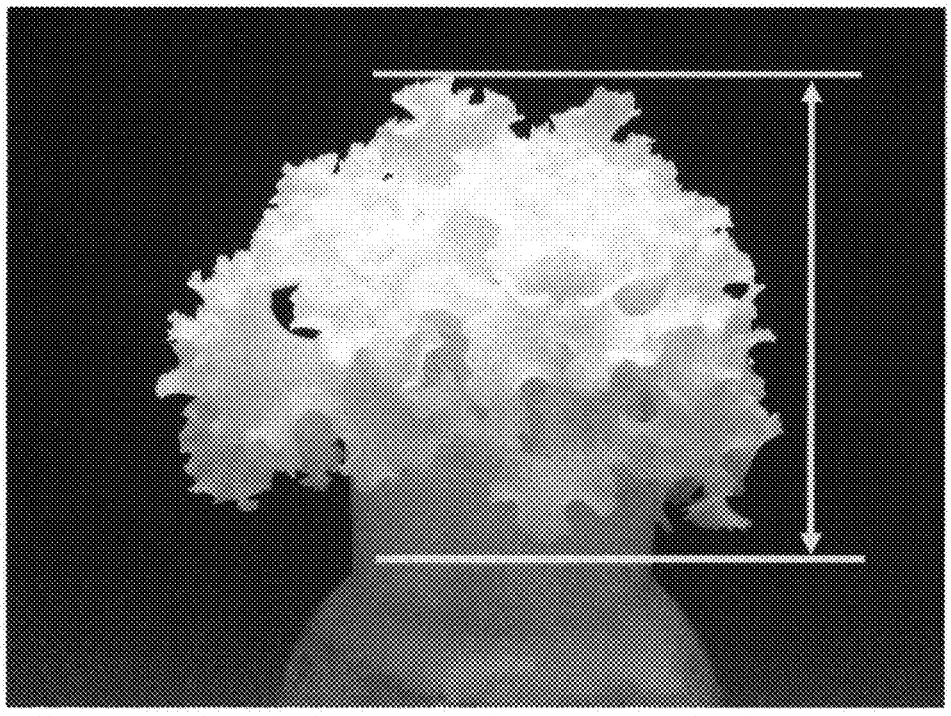
【FIG.15】
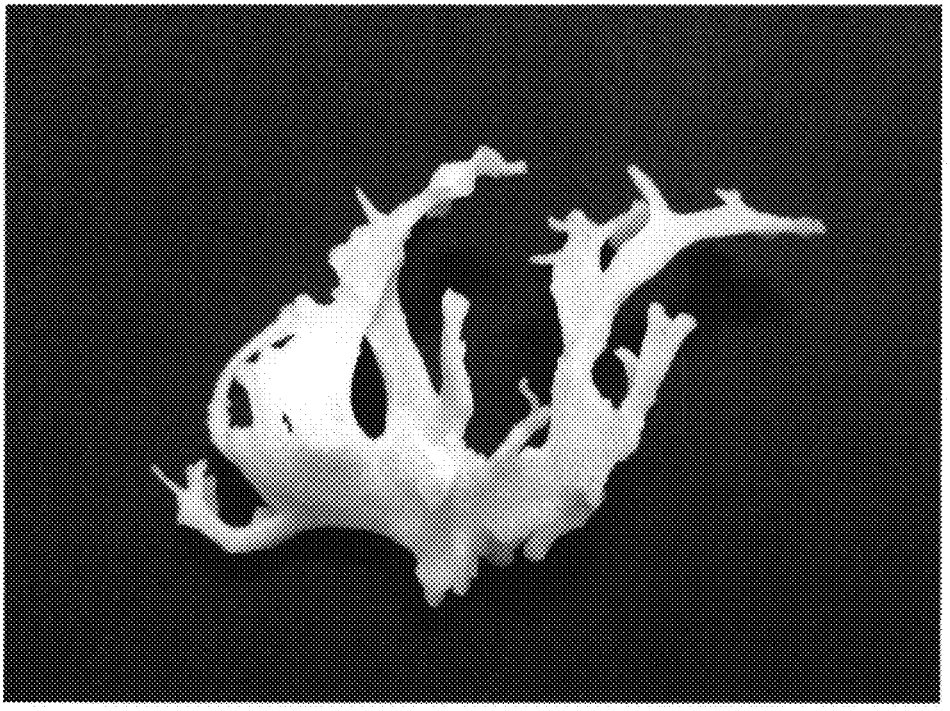

【FIG.16】
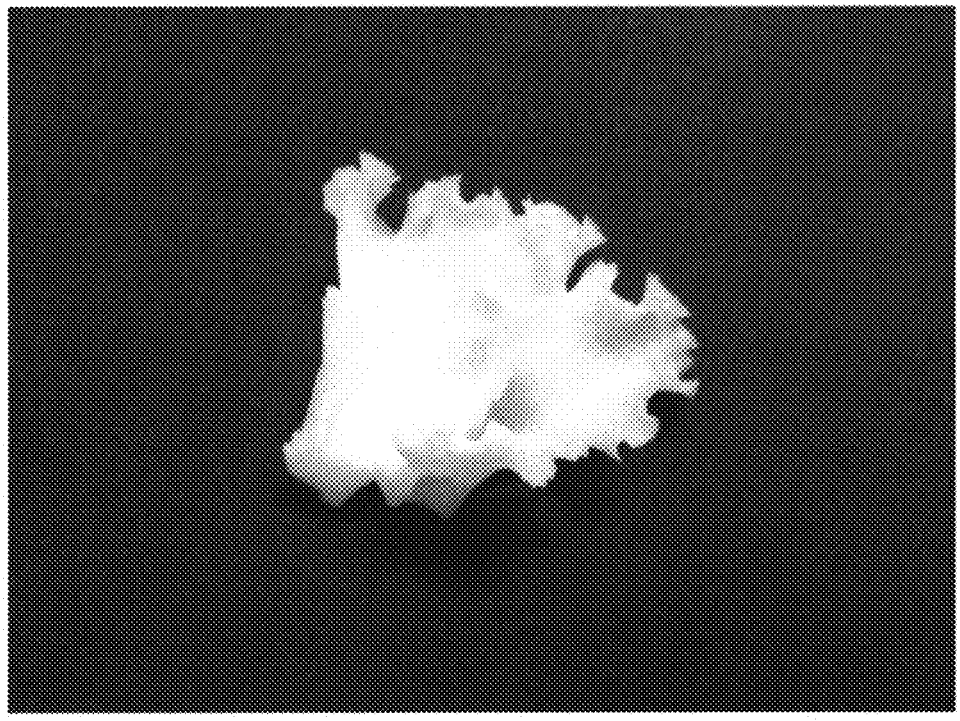
【FIG.17】
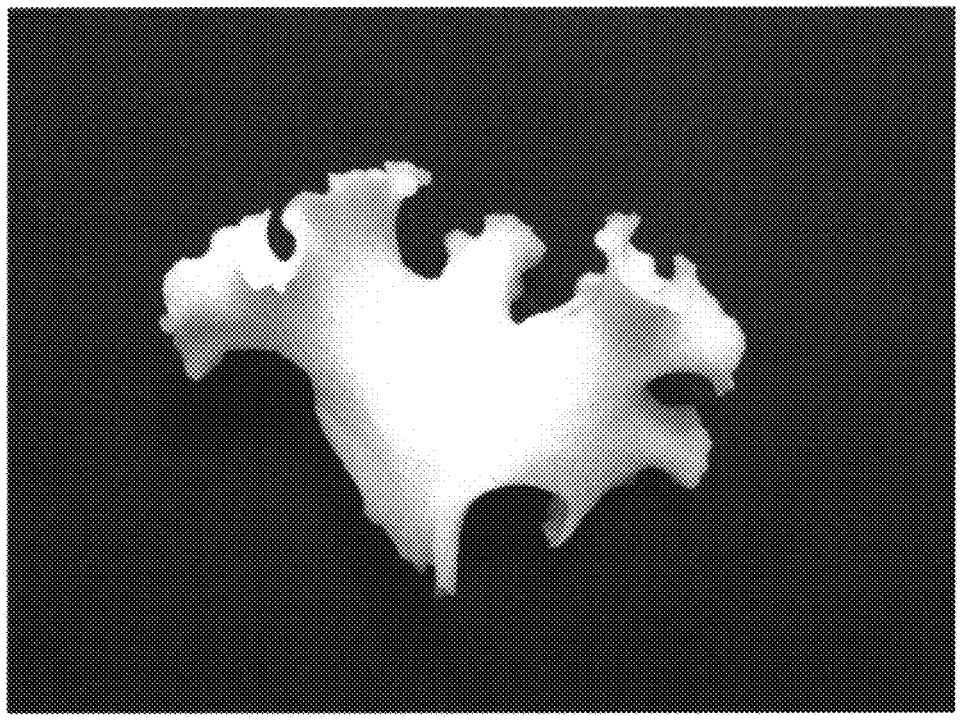

【FIG.18】
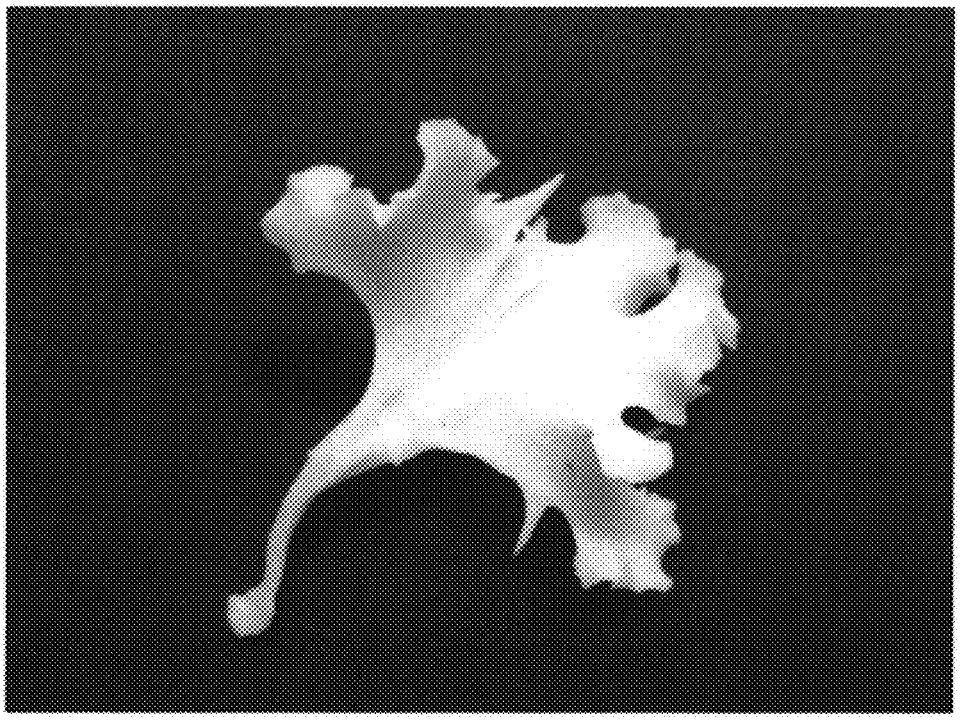
【FIG.19】
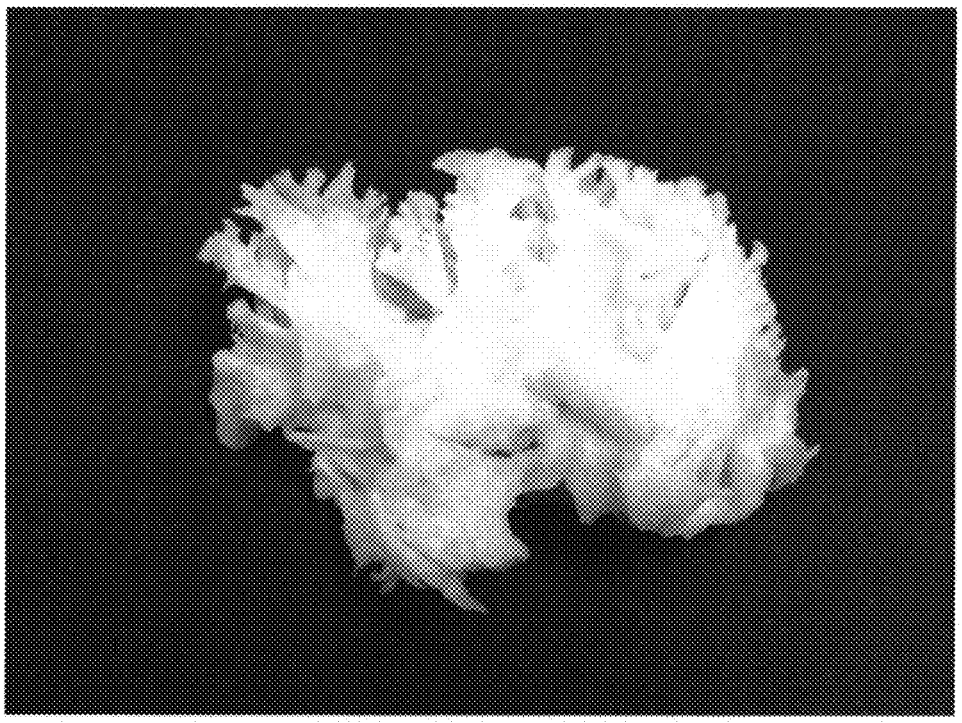

【FIG.20】
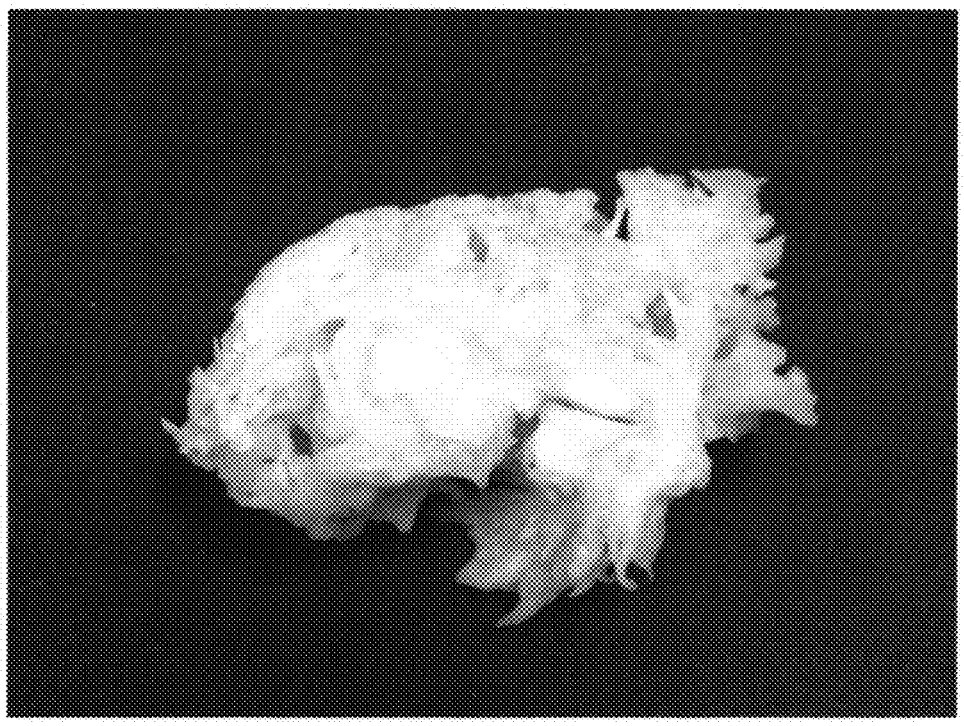
【FIG.21】
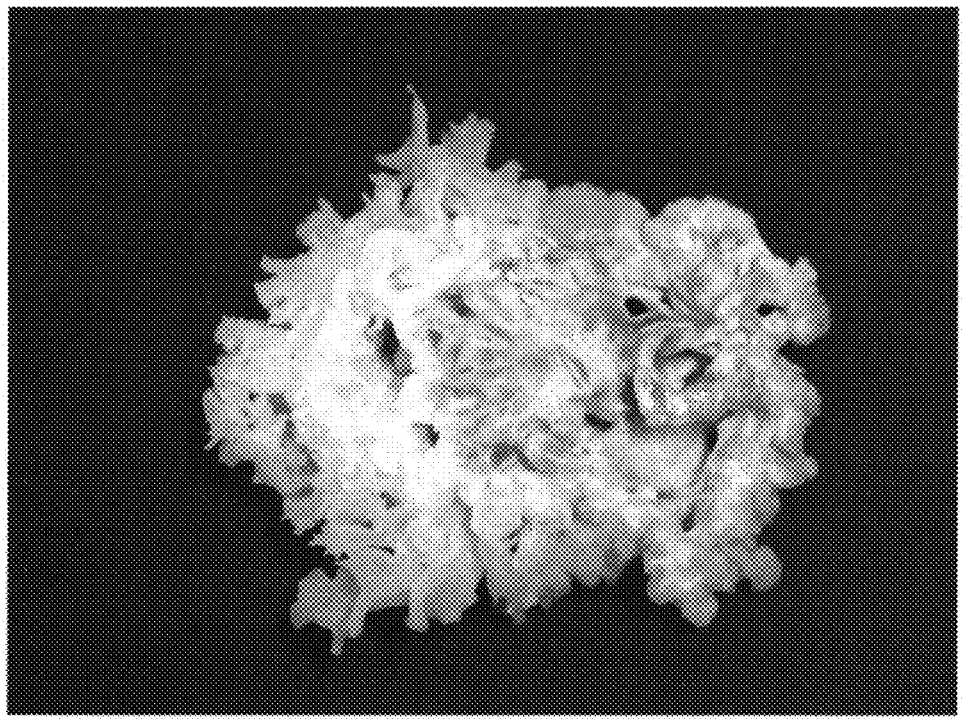

【FIG.22】
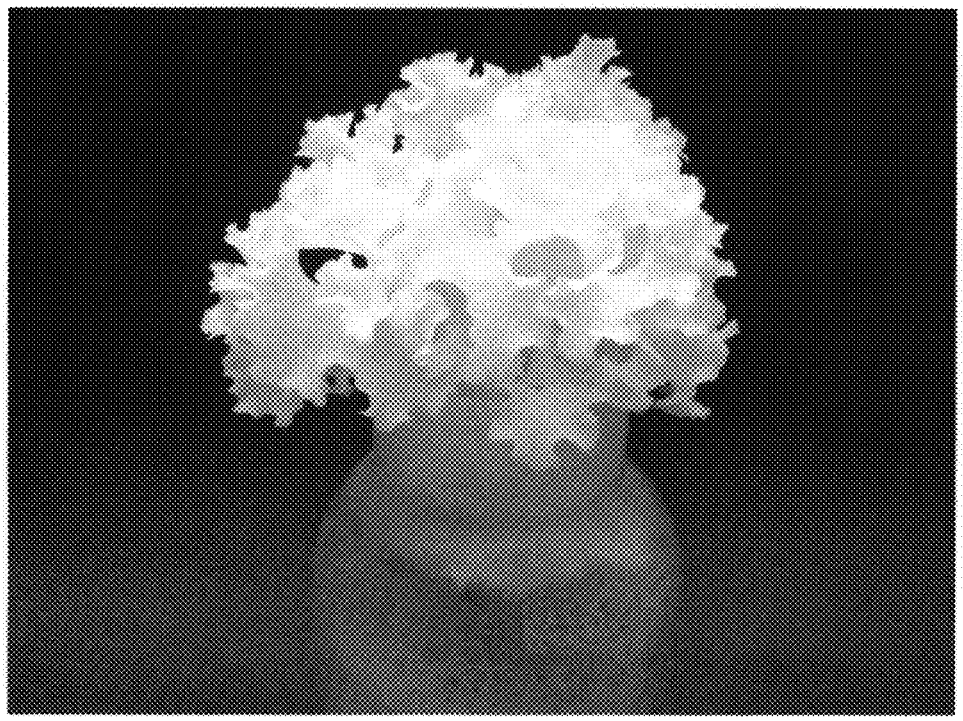
【FIG.23】
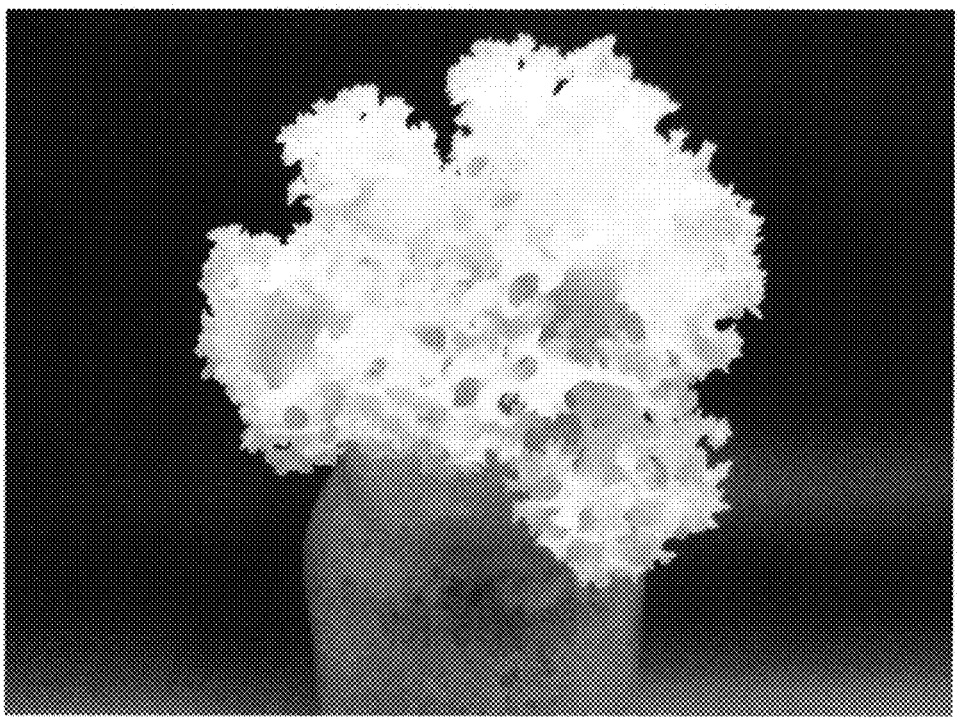

【FIG.24】
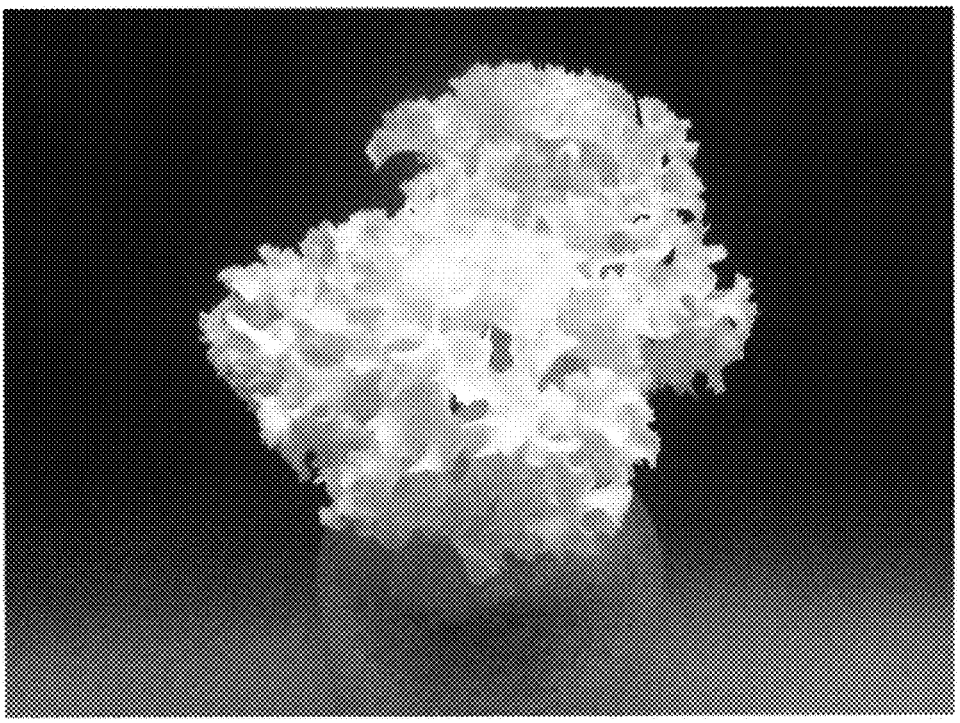
【FIG.25A】
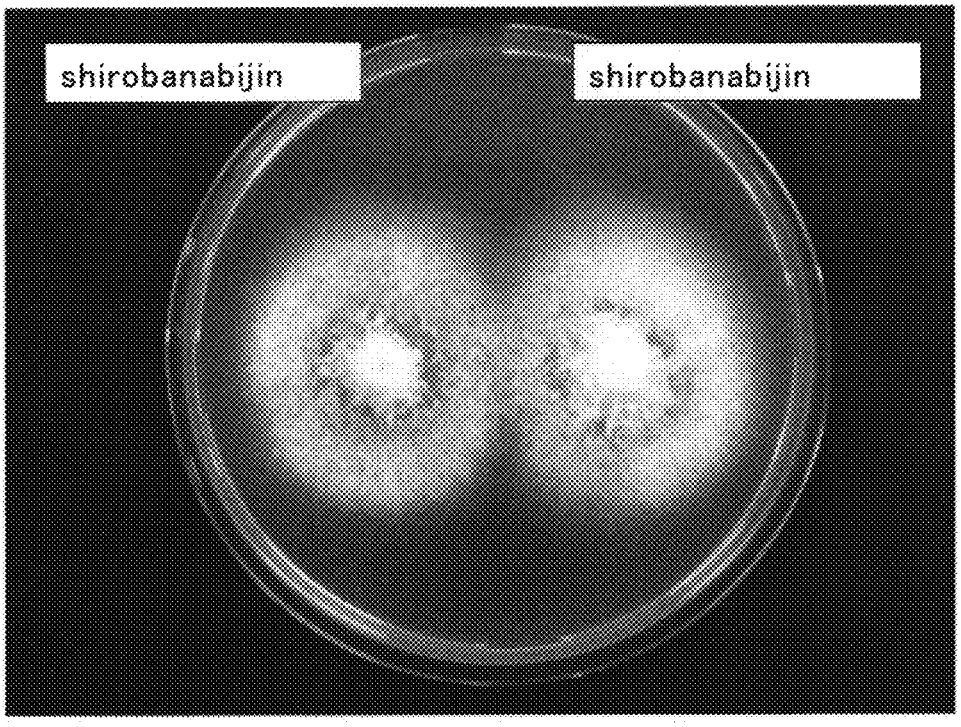

【FIG.25B】
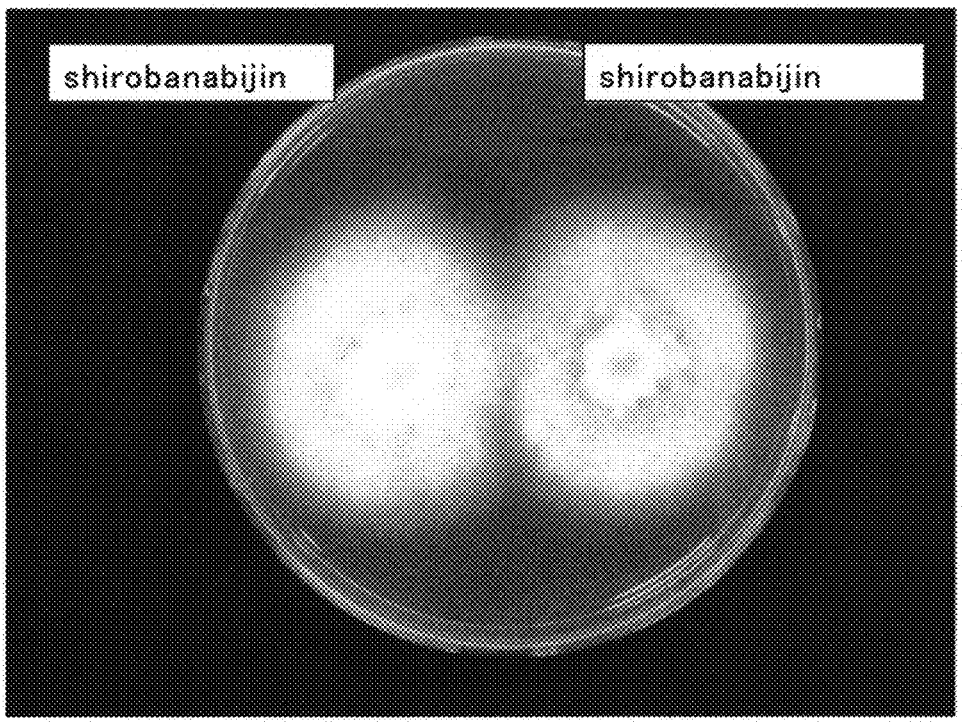
【FIG.26A】
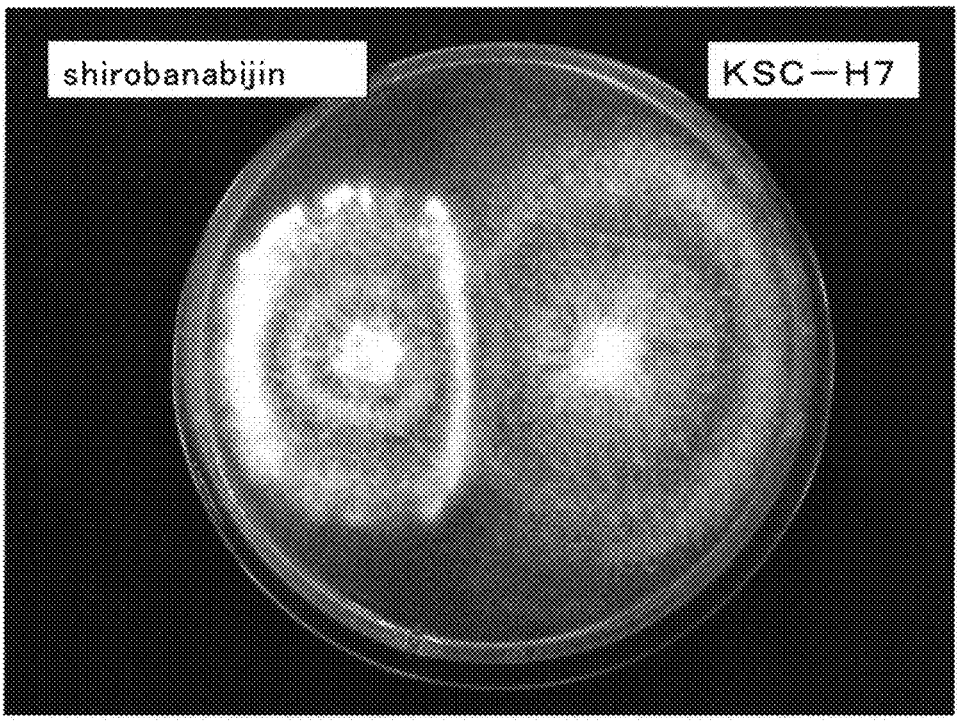

【FIG.26B】
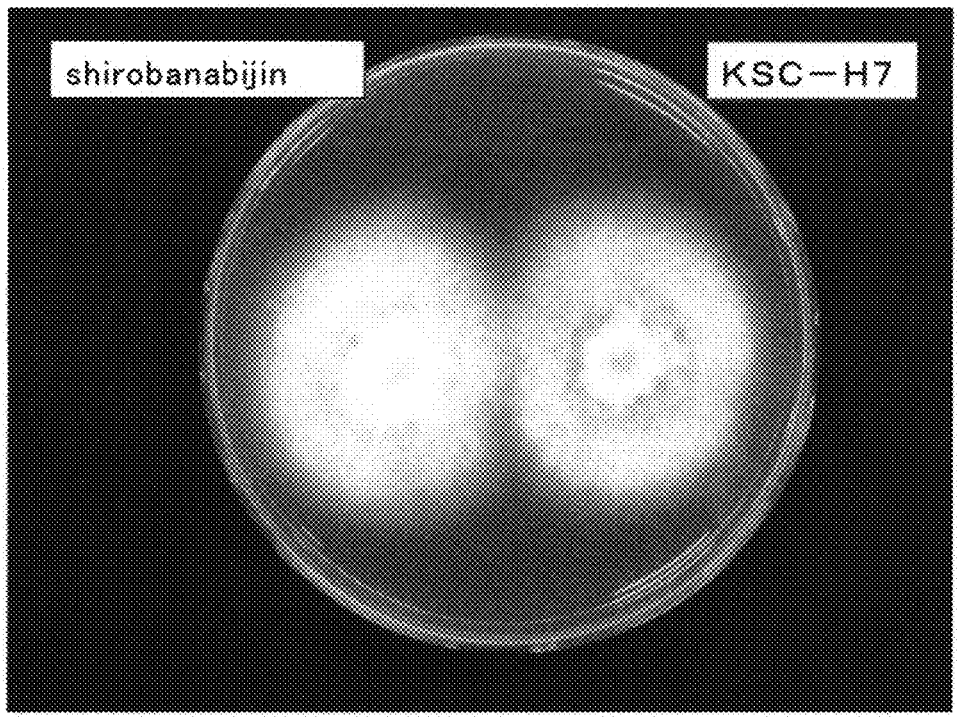
【FIG.27A】
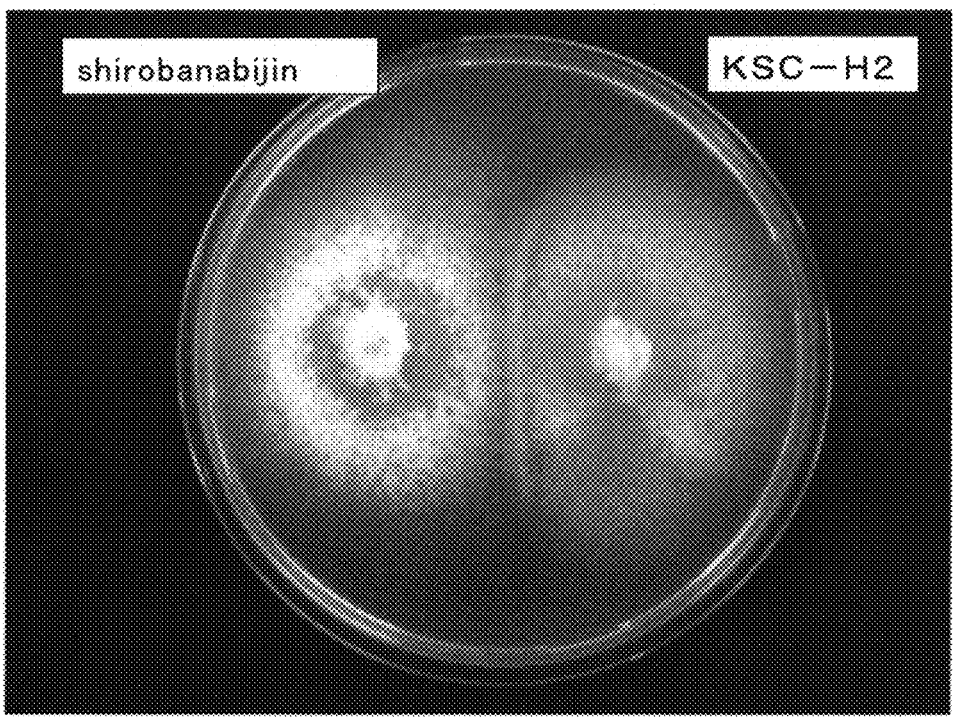

【FIG.27B】
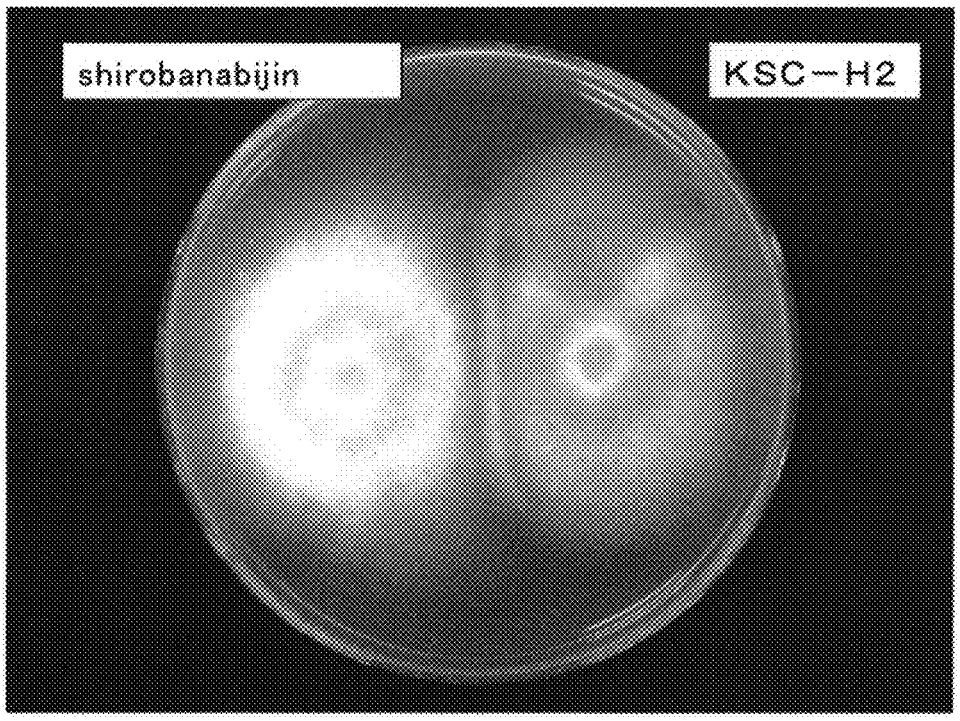

* * * * *